United States Patent [19]

Esanu

[11] Patent Number: 4,610,990

[45] Date of Patent: Sep. 9, 1986

[54] 5-(1-CYANO-1-ALKYL-N-METHYL-N-METHOXY-PHENETHYL)-ALKYLAMINO-2,2,8-TRIMETHYL-4H-DIOXINO-(4,5-c)-PYRIDINE DERIVATIVES, AND THEIR USE AS CALCIUM ANTAGONISTIC AGENTS

[75] Inventor: André Esanu, Paris, France

[73] Assignee: Societe de Conseils de Recherches et d'Applications Scientifiques (S.C.R.A.S.), Paris, France

[21] Appl. No.: 783,946

[22] Filed: Oct. 3, 1985

[30] Foreign Application Priority Data

Oct. 23, 1984 [GB] United Kingdom ............... 8426738

[51] Int. Cl.$^4$ ............... A61K 31/395; C07D 491/056
[52] U.S. Cl. ............................. 514/302; 546/115
[58] Field of Search ..................... 546/115; 514/302

[56]  References Cited

PUBLICATIONS

Newman et al., Alkylation of Nitriles: Ketenimine Formation, J. Am. Chem. Soc., vol. 82, pp. 873–875.
Rappoport, The Chemistry of the Cyano Group, p. 779.

Primary Examiner—Henry R. Jiles
Assistant Examiner—J. Richter
Attorney, Agent, or Firm—Lucas & Just

[57]  ABSTRACT

The invention relates to new 5-(1-cyano-1-alkyl-N-methyl-N-methoxy-phenethyl)-alkylamino-2,2,8-trimethyl-4H-dioxino-(4,5-c)-pyridine derivatives of the formula

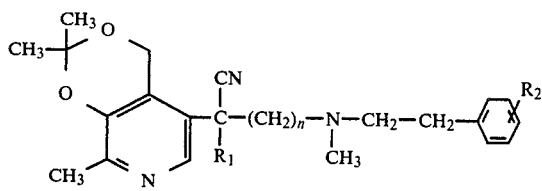

and therapeutically acceptable salts of these compounds, to a preparation process of the same comprising reacting, in stoichiometric proportions, the corresponding 5-(1-cyano-1-$R_1$)-methyl-2,2,8-trimethyl-4H-dioxino-(4,5-c)-pyridine of the formula

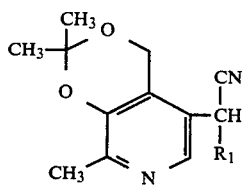

on the appropriate [N-methyl-N-(methoxy-phenethyl)]-ω-alkyl chloride of the formula

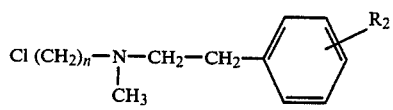

The invention relates also to therapeutic compositions containing said derivatives as active ingredients.

2 Claims, No Drawings

5-(1-CYANO-1-ALKYL-N-METHYL-N-METHOXY-PHENETHYL)-ALKYLAMINO-2,2,8-TRIMETHYL-4H-DIOXINO-(4,5-c)-PYRIDINE DERIVATIVES, AND THEIR USE AS CALCIUM ANTAGONISTIC AGENTS

The present invention relates to new derivatives of H-dioxino-(4,5-c)-pyridine, to a process for the preparation of the same and to therapeutic compositions, in which they are used as active ingredients.

More particularly, the invention relates to the 5-(1-cyano-1-alkyl-N-methyl-N-methoxy-phenethyl)-alkylamino-2,2,8-trimethyl-4H-dioxino-(4,5-c)-pyridine derivatives of the formula I

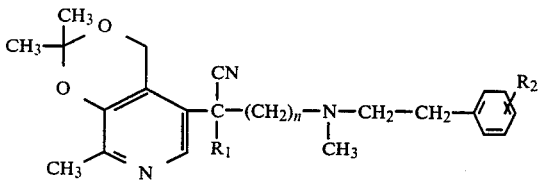

wherein n is an integer taking values from 2 to 5 included, $R_1$ stands for a straight or branched lower alkyl up to $C_5$ and $R_2$ stands for two or three $OCH_3$ groups, and to therapeutically acceptable salts of these compounds.

These compounds and their therapeutically acceptable salts are interesting as active ingredients for use in therapeutic compositions active as calcium antagonists. A toxicologic investigation has shown favourable $LD_{50}$ values on rats and mice per os and I.P.

The derivatives according to the invention may be readily prepared by reacting, in stoichiometric proportions, the corresponding 5-(1-cyano-1-$R_1$)-methyl-2,2,8-trimethyl-4H-dioxino-(4,5-c)-pyridine of the formula II

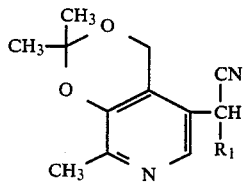

wherein $R_1$ is as above defined, on the appropriate [N-methyl-N-(methoxy-phenethyl)]-ω-alkyl chloride of the formula III

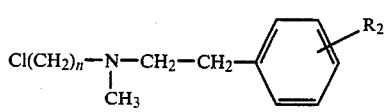

wherein n and $R_2$ are as above defined, in the presence of a stoichiometric amount of sodium hydride, in dimethylsulphoxide, at a temperature between 15° and 65° C.

For the obtention of compounds II, the starting material was the compund 5-hydroxymethyl 2,2,8-trimethyl-4H-dioxino-(4,5-c)-pyridine described in U.S. Pat. No. 3,717,636 further chlorinated by $SOCl_2$ (which gave 5-chloromethyl) and condensed with KCN (which gave 5-cyanomethyl); the starting material II, i.e. 5-(1-cyano)-alkyl was obtained by treating 5-cyanomethyl derivative by $R_1Br$ or $R_1Cl$ by the same process as hereunder described for the obtention of I from II and III.

The invention, finally, relates also to therapeutic compositions comprising as an active ingredient therein, an effective amount of one of the above defined compounds together with an appropriate diluent or carrier.

The invention will be better understood from the description of the following examples.

EXAMPLE 1

5-[1-cyano-1-methyl-N-methyl-N-(3,4-dimethoxy-phenethyl)]propylamino-2,2,8-trimethyl-4H-dioxino-(4,5-c)-pyridine $n = 2 \quad R_1 = methyl \quad R_2 = (OCH_3)_2$ In a one liter reactor fitted with cooling, warming and stirring means, were placed (after nitrogen cleaning of the apparatus) 4.9 g (0.1 mol) of 50% sodium hydride in oil and 100 ml of dimethylsulphoxide; the mixture was stirred and there was slowly added, dropwise, a solution of 23.2 g (0.1 mol) of 5-(1-cyano)-ethyl-2,2,8-trimethyl-4H-dioxino-(4,5-c)-pyridine dissolved in 150 ml of dimethylsulphoxide.

The reacting mixture darkened and temperature raised up to 30° C. Stirring was maintained for 30 minutes and there was slowly added 25.8 g (0.1 mol) of [N-methyl-N-(3,4-dimethoxyphenethyl)]-2-aminoethyl chloride dissolved in 100 ml of dimethylsulphoxide.

The reacting mixture was warmed at 50° C., stirred for 4 hours, poured on icy water and extracted by dichloromethylene. The organic phase was then washed with water, separated, dried, treated by carbon black, filtered and concentrated to dryness. The residue was thus treated by oxalic acid in 100 ml of acetone, which gave a yellow precipitate, separated, washed and recrystallized in methyl-ethyl-ketone. Yield 38.6 g (71%) of a yellow crystalline product melting at 164° C. (Tottoli), the analysis of which showed a perfect correspondence with the formula $C_{26}H_{35}N_3O_4$, $C_2H_2O_4$.

EXAMPLE 2

5-[1-cyano-1-n-propyl-N-methyl-N-(3,4,5-trimethoxy-phenethyl)]-n-propylamino-2,2,8-trimethyl-4H-dioxino-(4,5-c)-pyridine $n = 2 \quad R_1 = n\text{-propyl} \quad R_2 = (OCH_3)_3$ The method of example 1 was repeated but starting with 5-(1-cyano)-n-butyl-2,2,8-trimethyl-4H-dioxino-(4,5-c)-pyridine and [N-methyl-N-(3,4,5 - trimethoxy - phenethyl)]-2-aminoethyl chloride at 40° C., treatment was with hydrochloric acid. There was thus obtained 32.5 g (59%) of a pale yellow powder melting at 204° C. (Tottoli), the analysis of which showed a good correspondence with the formula $C_{29}H_{41}N_3O_5$, HCl.

EXAMPLE 3

5-[1-cyano-1-methyl-N-methyl-N-(3,4-dimethoxy-phenethyl)]-n-butylamino-2,2,8-trimethyl-4H-dioxino-(4,5-c)-pyridine $n = 3 \quad R_1 = methyl \quad R_2 = (OCH_3)_2$ The method of example 1 was repeated with the same pyridine derivative but with [N-methyl-N-(3,4-dimethoxy-phenethyl)]-3-amino-n-propyl chloride at 55° C. and final acidic treatment was omitted. There was thus obtained 29.5 g (63%) of a white product melting at 176°–178° C. (Tottoli), the analysis of which showed a perfect correspondence with the formula $C_{27}H_{37}N_3O_4$.

EXAMPLE 4

5-[1-cyano-1-ethyl-N-methyl-N-(3,4-dimethoxy-phenethyl)]-n-butylamino-2,2,8-trimethyl-4H-dioxino-(4,5-c)-pyridine $n = 3 \quad R_1 = \text{ethyl} \quad R_2 = (OCH_3)_2$ The method of example 3 was repeated but with 5-(1-cyano)-n-propyl-2,2,8-trimethyl-4H-dioxino-(4,5-c)-pyridine but at 50° C. There was thus obtained 25.2 g (52%) of a white powder melting at 197°–200° C. (Tottoli), the analysis of which showed a good correspondence with the formula $C_{28}H_{39}N_3O_4$.

EXAMPLE 5

5-[1-cyano-1-isopropyl-N-methyl-N-(3,4-dimethoxy-phenethyl)]-n-butylamino-2,2,8-trimethyl-4H-dioxino-(4,5-c)-pyridine $n = 3 \quad R_1 = \text{isopropyl} \quad R_2 = (OCH_3)_2$ The method of example 3 was repeated but with 5-(1-cyano-2-methyl)-n-propyl-2,2,8-trimethyl-4H-dioxino-(4,5-c)-pyridine and the same amine chloride, at 40° C. with a further acidic treatment by oxalic acid. There was thus obtained 40.5 g (69%) of a white crystalline powder melting at 185°–186° C. (Tottoli), the analysis of which showed a perfect correspondence with the formula $C_{29}H_{41}N_3O_4$, $C_2H_2O_4$.

EXAMPLE 6

5-[1-cyano-1-isopropyl-N-methyl-N-(3,4,5-trimethoxy-phenethyl]-n-butylamino-2,2,8-trimethvl-4H-dioxino-(4,5-c)-pyridine $n = 3 \quad R_1 = \text{isopropyl} \quad R_2 = (OCH_3)_3$ The method of example 5 was repeated but with [N-methyl-N-(3,4,5-trimethoxy-phenethyl)]-3-aminopropyl chloride, at 45° C. with a further acidic treatment by oxalic acid. There was thus obtained 45 g (73%) of a white crystalline powder melting at 170°–173° C. (Tottoli), the analysis of which showed a perfect correspondence with the formula $C_{30}H_{43}N_3O_5$, $C_2H_2O_4$.

EXAMPLE 7

5-[1-cyano-1-n-butyl-N-methyl-N-(3,4,5-trimethoxy-phenethyl)]-n-butylamino-2,2,8-trimethyl-4H-dioxino-(4,5-c)-pyridine $n = 3 \quad R_1 = \text{n-butyl} \quad R_2 = (OCH_3)_2$ The method of example 6 was repeated but with 5-(1-cyano)-n-pentyl-2,2,8-trimethyl-4H-dioxino-(4,5-c)-pyridine, and the same amine chloride, at 60° C. There was thus obtained 35.7 g (57%) of a white product melting at 144°–46° C. (Tottoli), the analysis of which showed a good correspondence with the formula $C_{31}H_{45}N_3O_5$, $C_2H_2O_4$.

EXAMPLE 8

5-[1-cyano-1-methyl-N-methyl-N-(3,4-dimethoxy-phenethyl)]-n-pentylamino-2,2,8-trimethyl-4H-dioxino-(4,5-c)-pyridine $n = 4 \quad R_1 = \text{methyl} \quad R_2 = (OCH_3)_2$ The method of example 3 was repeated with the safe pyridine derivative but with [N-methyl-N-(3,4-dimethoxy-phenethyl)]-4-amino-n-butyl chloride at 65° C. Yield was 30.8 g (64%) of a white product melting at 154°–55° C. (Tottoli), the analysis of which showed a good correspondence with the formula $C_{28}H_{39}N_3O_4$.

EXAMPLE 9

5-[1-cyano-1-n-pentyl-N-methyl-N-(3,4-dimethoxy-phenethyl)]-n-pentylamino-2,2,8-trimethyl-4H-dioxino-(4,5-c)-pyridine $n = 4 \quad R_1 = \text{n-pentyl} \quad R_2 = (OCH_3)_2$ The method of example 8 was repeated but with 5-(1-cyano)-n-hexyl-2,2,8-trimethyl-4H-dioxino-(4,5-c)-pyridine and the same amine chloride but at 45° C. and with a final acidic treatment by HCl. There was thus obtained 29.7 g (52%) of a white powder melting at 167°–169° C. (Tottoli), the analysis of which showed a good correspondence with the formula $C_{32}H_{47}N_3O_4$, HCl.

EXAMPLE 10

5-[1-cyano-1-ethyl-N-methyl-N-(3,4-dimethoxy-phenethyl)]-n-hexylamino-2,2,8-trimethyl-4H-dioxino-(4,5-c)-pyridine $n = 5 \quad R_1 = \text{ethyl} \quad R_2 = (OCH_3)_2$ The method of example 4 was repeated with the same pyridine derivative but with [N-methyl-N-(3,4-dimethoxy-phenethyl)]-6-amino-n-pentyl chloride at 35° C. Yield was 23.2 g (46%) of a pale yellow product melting at 193°–197° C. (Tottoli), the analysis of which showed a good correspondence with the formula $C_{30}H_{43}N_3O_4$.

EXAMPLE 11

5-[1-cyano-1-isopropyl-N-methyl-N-(3,4-dimethoxy-phenethyl)]-n-hexylamino-2,2,8-trimethyl-4H-dioxino-(4,5-c)-pyridine $n = 5 \quad R_1 = \text{isopropyl} \quad R_2 = (OCH_3)_2$ The method of example 10 was repeated but with 5-(1-cyano-2-methyl) n - propyl-2,2,8-trimethyl-4H-dioxino-(4,5-c)-pyridine and the same amine chloride at 30° C., with a further acidic treatment by oxalic acid. There was thus obtained 39.6 g (65%) of a white crystalline product melting at 144° C. (Tottoli), the analysis of which showed a very good correspondence with the formula $C_{31}H_{45}N_3O_4$, $C_2H_2O_4$.

EXAMPLE 12

5-[1-cyano-1-n-butyl-N-methyl-N-(3,4,5-trimethoxy-phenethyl)]-n-hexylamino-2,2,8-trimethyl-4H-dioxino-(4,5-c)-pyridine n = 5   $R_1$ = n-butyl   $R_2$ = $(OCH_3)_3$ The method of example 7 was repeated but with [N-methyl-N-(3,4,5-trimethoxy-phenethyl)]-6-amino-n-pentyl chloride at 40° C., with a further acidic treatment by oxalic acid. There was thus obtained 38.1 g (58%) of a white crystalline product melting at 131° C. (Tottoli), the analysis of which showed a very good correspondence with the formula $C_{33}H_{49}N_3O_5$, $C_2H_2O_4$.

TOXICITY

Per os $LD_{50}$ of the compounds of the invention, determined on mice, is from 450 mg/kg and over. For purpose of comparison, the reference compound Verapamil (DCI) has a $LD_{50}$ of 150 mg/kg. Cardiotoxicity on anaesthetized dogs starts at 3 mg/kg IV whereas Verapamil is cardiotoxic at 1 mg/kg.

PHARMACOLOGY

The interest of the compounds of the invention has been evidenced by various tests.

(A) Isolated rabbit aorta strips treated by various contracturing agents.

This experiment was conducted according to the lines of the methods described by FURCHGOTT R. F. and BHADRAKOM S. - Reactions of strips of rabbit aorta to epinephrine, isopropylarterenol, sodium nitrite and other drugs. J. Pharmac. Exp. Therapeut., 1953, 108, 129–143, VAN ROSSUM J. M., Arch. Int. Pharmacodyn. Ther., 1963, 143, 299–330 and ARUNLAKSHANA, O. and SCHILD, H. O., 1959, Brit. J. Pharmac. 14, 48–58, using noradrenaline (NE), serotonine (5-HT), histamine (HIST), KCl and angiotensine II as agonists.

The compounds of the invention were compared to Verapamil on these agonists and showed a similar range of action, with significative and generally comparable values of $PA_2$ (for NE, 5-HT and HIST) or of $IC_{50}$ (for KCl or angiotensine); however, they appear 5 to 10 times more active on 5-HT (average value for the compounds of the invention: $1.1 \times 10^{-8}$ and $7. \times 10^{-8}$ for Verapamil). These compounds are competitive antagonists of the 5-HT receptor.

(B) Experimental ulcer induced by dimaprit.

15 batches of each 5 male Sprague Dawley rats (150–200 g) were treated as follows:

Batches 1–12: The rats of each of these batches received 25 mg/kg per os of one of the compounds of the invention, suspended in 1 ml of physiologic serum.

Batches 13 and 14: The rats of these batches received 1 ml of physiologic serum.

Batches 15: The rats of this batch received 25 mg/kg of ramitidine, as reference compound, suspended in 1 ml of physiologic serum.

30 minutes after this administration, all batches, except batch 13, received, IP, 175 mg/kg of dimaprit $(NH_2-(CNH)-(CH_2)_3-N(CH_3)_2)$.

Four hours after this treatment, the animals were killed and the ulcers counted. Batch 13 was a blank control and batch 14 the ulceration control. Results were given in percentage of protection compared with ulceration control. Protection by ramitidine was 39%, whereas protection for the compounds of the invention was comprised between 39 and 46,5%.

PRESENTATION - POSOLOGY

For oral use, the compounds of the invention may be presented in 50 mg dosage units associated with an appropriate diluent or carrier, in tablet, gelatine capsules or in suspension - Posology is of 1 or 2 units per diem.

For IV route, phials contain 10 mg of active compound and posology is 1 or 2 phials per diem.

Indications are angor, vasospasms and headaches.

I claim:

1. 5-(1-cyano-1-alkyl-N-methyl-N-methoxy-phenethyl)alkylamino-2,2,8-trimethyl-4H-dioxino-(4,5-c)-pyridine derivatives of the formula

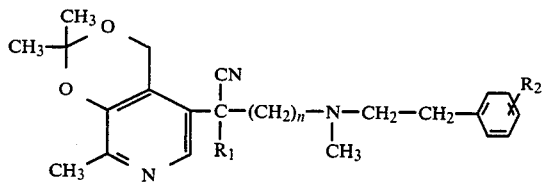

wherein n is an integer taking values from 2 to 5 included, $R_1$ stands for a straight or branched lower alkyl up to $C_5$ and $R_2$ stands for two or three $OCH_3$ groups and therapeutically acceptable salts of these compounds.

2. A therapeutic composition comprising as an active ingredient therein, an amount effective to act as a calcium antagonist of a compound according to claim 1 together with an appropriate diluent or carrier.

* * * * *

UNITED STATES PATENT AND TRADEMARK OFFICE
CERTIFICATE OF CORRECTION

PATENT NO. : 4,610,990
DATED : September 9, 1986
INVENTOR(S) : Andre Esanu

It is certified that error appears in the above-identified patent and that said Letters Patent is hereby corrected as shown below:

Column 1, line 9, before "H-dioxino" insert --4--.

Column 1, line 62, after "5-hydroxymethyl" and before "2,2,8" insert a hyphen.

Column 3, line 42, change "trimethvl" to --trimethyl--.

Column 3, line 67, after "white" insert --crystalline--.

Column 4, line 12, change "safe" to --same--.

Column 4, line 62, after "(1-cyano-2-methyl)" and before "n" insert a hyphen.

Column 5, line 37, before "108" insert --Vol.--; line 38, before "143" insert --Vol.--; line 40, before "14" insert --Vol.--.

Column 6, line 30, change "angor" to --anger--.

Signed and Sealed this

Seventh Day of April, 1987

*Attest:*

DONALD J. QUIGG

*Attesting Officer*   *Commissioner of Patents and Trademarks*